United States Patent [19]
Kennedy

[11] Patent Number: 6,077,683
[45] Date of Patent: Jun. 20, 2000

[54] METHOD OF SYNTHESIS OF DESULFATED HEPARIN AND USE THEREOF FOR INHIBITION OF ELASTASE AND CATHEPSIN

[75] Inventor: Thomas P. Kennedy, Richmond, Va.

[73] Assignee: Carolinas HealthCare System, Charlotte, N.C.

[21] Appl. No.: 09/332,820

[22] Filed: Jun. 14, 1999

Related U.S. Application Data

[60] Division of application No. 08/865,211, May 29, 1997, Pat. No. 5,912,237, which is a continuation-in-part of application No. 08/191,436, Feb. 3, 1994, Pat. No. 5,668,118, which is a continuation-in-part of application No. 08/185,069, Jan. 21, 1994, abandoned, which is a continuation-in-part of application No. 07/919,309, Jul. 24, 1992, abandoned.

[51] Int. Cl.$^7$ .............................. C12Q 1/37; C12Q 1/00
[52] U.S. Cl. .................... 435/23; 435/4; 536/21; 514/56
[58] Field of Search ............................ 435/23, 4; 536/21; 514/56

[56] References Cited

U.S. PATENT DOCUMENTS

| | | | |
|---|---|---|---|
| 4,816,446 | 3/1989 | Feller et al. | 435/23 |
| 5,296,471 | 3/1994 | Holme et al. | 435/23 |
| 5,668,118 | 9/1997 | Kennedy | 514/56 |
| 5,912,237 | 6/1999 | Kennedy | 514/56 |

FOREIGN PATENT DOCUMENTS

| | | |
|---|---|---|
| 0 140 781 A2 | 8/1985 | European Pat. Off. |
| 0 208 623 A3 | 11/1986 | European Pat. Off. |
| 0 380 943 A1 | 8/1990 | European Pat. Off. |
| 0 557 887 A2 | 12/1993 | European Pat. Off. |

OTHER PUBLICATIONS

L. Levy et al., "Chemical and Pharmacological Studies on N–Sulfated Heparin", *Proc. Soc. Exp. Biol. and Med.*, 109:901–905 (1962).

F. Redini et al., "Influence of Heparin Fragments on the Biological Activities of Elastase(s) and Alpha$_1$ Proteinase Inhibitor", *Biochem. Pharmacol.*, 37:4257–5261 (1988).

F. Redini et al., "Inhibition of Leukocyte Elastase by Heparin and its Derivatives", *Biochem. J.*, 252:515–519 (1988).

M. Jaseija et al., "Novel Regio–and Stereoselective Modifications of Heparin in Alkaline Solution. Nuclear Magnetic Resonance Spectroscopic Evidence", *Can. J. Chem.*, 67:1449–1456 (1989).

E. Sache et al., "Partially N–Desulfated Heparin as a Non–Anticoagulant Heparin: Some Physico–Chemical and Biological Properties", *Thromb. Res.*, 55:247–258 (1989).

N.V. Rao et al., "Sulfated Polysaccharides Prevent Human Leukocyte Elastase–Induced Acute Lung Injury and Emphysema in Hamsters", *Am. Rev. Respir. Dis.*, 142:407–412 (1990).

T. Irimura et al., "Chemically Modified Heparins as Inhibitors of Heparan Sulfate Specific Endo–β–glucuronidase (Heparanase) of Metastiatic Melanoma Cells", *Biochemistry*, 25:5322–5328 (1986).

Nagasawa et al., "Hydrophobic–Interaction Chromatography of Glycosaminoglycuronans", *Carb. Res.* 111:273–281 (1983).

*Primary Examiner*—Louise N. Leary
*Attorney, Agent, or Firm*—Alston & Bird LLP

[57] ABSTRACT

A method and medicament for the inhibition of neutrophil elastase and cathepsin G in mammals comprising administering a treatment effective amount of 2-O-desulfated heparin to a mammal in need thereof. The medicament preferably is administered by aerosolization or by intravenous (IV) injection. Preferably, the 2-O-desulfated heparin medicament includes a physiologically acceptable carrier which may be selected from the group consisting of physiologically buffered saline, normal saline, and distilled water. Additionally provided is a method of synthesizing 2-O-desulfated heparin.

26 Claims, 6 Drawing Sheets

METHOD OF SYNTHESIS OF DESULFATED HEPARIN AND USE THEREOF FOR INHIBITION OF ELASTASE AND CATHEPSIN

RELATED APPLICATIONS

This application is a divisional of U.S. patent application Ser. No. 08/865,211, filed May 29, 1997, now U.S. Pat. No. 5,912,237, which is a continuation-in-part of U.S. patent application Ser. No. 08/191,436, filed Feb. 3, 1994, issued as U.S. Pat. No. 5,668,118, which is a continuation-in-part of U.S. patent application Ser. No. 08/185,069, filed Jan. 21, 1994, abandoned, which is a continuation-in-part of U.S. patent application Ser. No. 07/919,309, filed Jul. 24, 1992, abandoned.

BACKGROUND OF THE INVENTION

1. Field of the Invention

The present invention relates to medical treatment of mammals and more specifically to methods and medicaments for the control of neutrophil elastase and cathepsin G in mammals. Additionally, the present invention relates to methods of synthesis of 2-O-desulfated heparin, a medicament useful for the control of neutrophil elastase and cathepsin G in mammals.

2. Background Art

Activated neutrophils play an important role in a number of human and other mammalian diseases by releasing a number of oxidant chemicals and enzymes after migration into an affected organ. While oxidants, such as superoxide anion, hydrogen peroxide and hypochlorous acid are injurious by themselves, the major destructive elements produced by activated neutrophils are cationic proteases, the bulk of which consist of elastase and cathepsin G. When neutrophils release these proteases, tissue destruction occurs unless the proteases are neutralized by sufficient extracellular anti-proteinases such as α-1-anti-proteinase.

Individuals with an inherited deficiency of α-1-anti-proteinase suffer unimpeded proteolytic lung destruction over a lifetime, resulting ultimately in the development of pulmonary emphysema Cigarette smoking causes the influx of activated leukocytes into the lung, with subsequent degranulation and /release of proteases. Cigarette derived oxidants also inactivate α-1-anti-proteinase by oxidizing an important methionine near the active site. Elastase delivered to the alveolar lung unit as a result of the influx due to cigarette smoking, concurrent with oxidative inactivation of α-1-anti-proteinase activity, produces an imbalance of protease/anti-proteinase activity that is thought to be a major cause of human emphysema from cigarette smoking.

When the imbalance occurs within the airway, chronic airway inflammation is the result, and neutrophil derived elastase and cathepsin G are thought important in the pathogenesis of chronic bronchitis. If the imbalance occurs within the pulmonary vasculature, the resulting microvascular injury causes lung edema formation. In this fashion the influx of activated leukocytes and release of elastase and other neutrophil proteases are major causes of lung injury in the Adult Respiratory Distress Syndrome. Neutrophil derived elastase is also an important cause of proteolytic lung destruction in cystic fibrosis, a disease characterized by intense mucopurulent bronchitis and some of the highest levels of elastase activity measured in any human disease.

Also, diseases such as myocardial infarction and stroke, caused by sudden loss of organ blood flow, followed by blood flow restoration (ischemia-reperfusion injury) are characterized by magnification of tissue destruction during the reperfusion phase when activated leukocytes rapidly invade the already injured tissue. Neutrophil elastase delivered to ischemic reperfused organs has been demonstrated to play a pivotal role in the pathogenesis of reperfusion injury of the myocardium, bowel and other tissues. The role of cathepsin G in the processes above is not as well studied, but may be equally important, since there is twice as much cathepsin G present in the neutrophil as elastase.

Because elastase and cathepsin G are mediators of a variety of important human diseases, developing effective inhibitors of these enzymes is an active goal in experimental pharmacology. However, to date, no completely effective and safe inhibitor of both elastase and cathepsin G has been reported. A small organic inhibitor of elastase has been developed (C. P. Sommerhoff, et al., *European Journal of Pharmacology* (1991) 193:153–158), but it failed to demonstrate activity against cathepsin G. Two biomolecules, α-1-anti-proteinase inhibitor and bronchial secretory inhibitor, are sensitive to inactivation by neutrophil oxidants and are not likely to be effective in biologic environments where neutrophil oxidants and proteases are present simultaneously (D. C. Flenley, *Quarterly Journal of Medicine* (1986) 61:901–909; C. Vogelmeier, et al., *Journal of Clinical Investigation* (1991) 87:482–488). An inhibitor is needed which is simultaneously effective against both elastase and cathepsin G but is impervious to either proteolytic or oxidative inactivation. The sulfated polysaccharides have each of those desirable qualities.

It has been previously reported that heparin and other sulfated polysaccharides are potent non-competitive inhibitors of elastase and cathepsin G from human polymorphonuclear leukocytes (N. V. Rao, et al., A. M. *Rev. Respir. Dis.* (1990) 142:407–412; A Baichi, et al., *Biochem. Pharmacol.* (1980) 29:1723–1727; A. Baichi, et al., *Biochem. Pharmacol.* (1981) 30:703–708; K. Marossy, *Biochim.Biophys. Acta*, (1981) 659:351–361; A. Baichi, et al., *Chem Biol Interactions* (1984) 51:1–11; A. Lutini, et al., *Biochem. Int.* (1985) 10:221–232; F. Redini, et al., *Biochem. J.* (1988) 252:515–519; and F. Redini, et al., *Biochem Pharmacol.* (1988) 37:4257–4261.) It is believed that the basis for inhibition is by formation of electrostatic bonds between the negatively charged sulfate groups of the polysaccharide and the positively charged guanidinium groups of the arginine residues located at the surface of those highly basic enzymes such as elastase or cathepsin G. The interaction does not influence the active center of the enzyme but causes an indirect loss of elastolytic activity.

Of all the sulfated polysaccharides, heparin has the longest and safest history of use in man. From a toxicologic consideration, heparin is the most desirable inhibitor of elastase and cathepsin G but for the fact that it is an anti-coagulant even when delivered selectively to the lung by aerosol. It is believed that heparin acts as an anti-coagulant because of a repeated sequence of saccharides which binds specifically to the plasma protein anti-thrombin III, dramatically accelerating the rate at which anti-thrombin inhibits the procoagulant effect of thrombin on the cascade of blood coagulation. Only a portion of commercial heparin binds to anti-thrombin III, and passage of heparin over an affinity column of anti-thrombin III-sepharose removes the anti-coagulant fraction leaving an incompletely sulfated fraction devoid of anti-coagulant activity. However, utilizing this process to rid heparin of its anti-coagulant activity is too inefficient to be undertaken on a commercially practical scale.

Previously, it has been noted that the activity of a polysaccharide as an inhibitor of human polymorphonuclear leucocyte elastase (HlE) and cathepsin G is directly dependent upon the presence of intact sulfate groups. Dextran sulfate is a potent inhibitor of elastase, but non-sulfated dextran is not. Furthermore, the available literature suggests that even partial desulfation of polysaccharides eliminates inhibitory activity toward HLE and cathepsin G while chemical over-sulfation enhances inhibitory activity. The importance of sulfate groups was studied using fragments of heparin obtained by chemical depolymerization with $HNO_2$ followed by gel filtration (F. Redini, et al., *Biochem. J.*, (1988) 252:515–519). Unmodified heparin fragments obtained by this latter process were potent inhibitors of elastase but retained their strong anticoagulant power. Increasing the degree of sulfation by chemical O-sulfation of the fragments markedly increased their potency as elastase inhibitors but did not materially alter the anticoagulant activity of the fragments. On the other hand, N-desulfation followed by N-acetylation (to cover the remaining positive charge and reduce the anticoagulant activity of the fragments) completely eliminated inhibitory activity toward human leukocyte elastase and cathepsin G (Redini et al.). Chemical over-O-sulfation of the N-desulfated fragments not only restored inhibitory activity but gave the fragments higher inhibitory potential compared to their original counterparts with a similar degree of sulfation but containing N-sulfate groups. It has been suggested that not only was the degree of sulfation important to inhibitory activity, but that the presence of O-sulfates were more important than the presence of N-sulfates (Redini et al.). However, none of these highly effective, modified heparins were suitable for use in mammals due to their potent continuing anticoagulant activity.

Several chemical methods exist for inactivating heparin as an anti-coagulant. Most are based on techniques of chemical desulfation, since it is well established that degree of sulfation is an important determinant of anticoagulant activity.

N-desulfation by treatment of the pyridinium heparin salt with dimethylsulfoxide (DMSO) in five percent methanol for 1.5 hours at 50° C. and total desulfation by similar treatment in DMSO in 10% methanol for 18 hours at 100° C. are commonly used chemical modifications to remove anti-coagulant activity from heparin. Another method to remove anti-coagulant activity from heparin is acid hydrolysis at 55–60° C. for 72 hours to produce partial N-desulfation. However, removal of all sulfates or even a partial desulfation by removal of N-sulfates inactivates heparin and other sulfated polysaccharides as inhibitors of human elastase and cathepsin G. Thus, the art teaches that currently utilized desulfation methods which remove anti-coagulant activity of heparin also destroy its ability to inhibit cationic leukocyte proteases such as elastase and cathepsin G.

Moreover, the art demonstrates that over-sulfation leads to increased activity against elastase and cathepsin G with continuing anticoagulant activity while desulfation leads to decreased anticoagulant activity with greatly diminished activity against elastase and cathepsin G. In contrast to what would be predicted by the prior art, the present invention provides that selective 2-O-desulfation of α-L-iduronic acid-2-sulfate eliminates the anticoagulant activity of heparin without destroying the activity of the modified heparin as an inhibitor of elastase and cathepsin G.

Heparin has been widely used as a blood anticoagulant. However, it has also been widely recognized that there is a lack of uniform anticoagulant activity among different heparins (M. Jaseja et al., "Novel regio- and stereoselective modifications of heparin in alkaline solution. Nuclear magnetic resonance spectroscopic evidence," *Can. J. Chem.*, 67:1449–1456 (1989)). Therefore, studies have been made of the anticoagulant activity of heparin (Jaseja et al. and R. Rej et al, "Importance for Blood Anticoagulant activity of a 2-Sulfate Group on L-Iduronic Acid Residues in Heparin," *Thrombosis and Hemostasis*, 61(3):540 (1989). Both references, in studying variations of heparin disclose the preparation of a previously unreported compound, 2-O-desulfated heparin. Briefly, the Rej et al. and Jaseja et al. method starts with a solution of heparin in 0.1 N sodium hydroxide which is then lyophilized, thereby effecting a selective displacement of the 2-sulfate group of α-L-iduronic acid 2-sulfate and leaving a 2-O-desulfated α-L-iduronic acid residue. This compound was shown to have minimal anticoagulant activity. No suggestion of elastase or cathepsin G inhibition or any uses requiring elastase or cathepsin G inhibition were made in these studies. Therefore, Rej et al and Jaseja et al. found no activity for 2-O-desulfated heparin and thus did not disclose any effective doses for the compound for any use.

In their report of the chemistry of removing 2-O-sulfate from alpha-L-iduronic acid 2-sulfate, Jaseja et al., describe that alpha-L-iduronic acid 2-sulfate is converted to alpha-L-iduronic acid in a two-step process. First, selective displacement of the 2-O-sulfate group occurs, with formation of a 2,3-anhydro intermediate. The 2,3-anhydro intermediate is then further hydrolyzed to alpha-L-iduronic acid. Specifically, Jaseja et al., teach that 40 mg of beef lung heparin was added to 10 ml water. When this 0.4% solution was alkalinized with 0.1 N sodium hydroxide to pH 11.2 to 11.5 and lyophilized, the 2,3-anydro intermediate was quantitatively formed. By their methods, when the pH of the solution was raised further to 12.5 to 12.8, further hydrolysis of the intermediate occurred, with quantitative formation of desulfated alpha-L-iduronic acid. Jaseja et al., demonstrate that diminished antithrombin III binding affinity is conferred by loss of the 2-O-sulfate, since both the 2,3-anhydro intermediate and fully hydrolyzed alpha-L-iduronic acid modifications had substantially decreased anticoagulant activity compared to the starting heparin. Thus, Jaseja et al, provides explicit instructions for a laboratory scale reaction to produce small quantities of 2-O-desulfated heparin by alkaline hydrolysis during lyophilization.

The present invention involves the surprising discovery that 2-O-desulfated heparin has elastase and cathepsin G inhibition activity. This activity was unexpected since, as discussed above, prior desulfation attempts that resulted in a decreased anticoagulant activity also resulted in a lack of elastase and cathepsin G inhibition activity. Thus, the novel use of 2-O-desulfated heparin to inhibit elastase and cathepsin G provides a solution to a long-felt problem in the art.

Additionally, applicants also unexpectedly discovered that, when the method of Jaseja et al. was performed on a commercially feasible scale, the compounds thus produced possessed significantly less elastase inhibitory activity then the compounds produced by their published small-scale method. The present invention therefore provides an effective method of producing 2-O-desulfated heparin in commercially useful quantities.

SUMMARY OF THE INVENTION

It is an object of the present invention to provide a method for inhibiting elastase and cathepsin G in mammals. It is another object of the present invention to provide such inhibition in a therapeutic agent which substantially does not induce anti-coagulant activity. It is a further object of the present invention to provide a method for inhibiting elastase and cathepsin G by aerosol treatment or intravenous (IV) administration of the therapeutic agent. Another object of the instant invention is to provide a method of synthesizing 2-O desulfated heparin. It is an advantage of the present invention that the method provides a therapeutic agent which substantially inhibits elastase and cathepsin G without inducing anticoagulant activity. It is a further advantage of the present invention that the therapeutic agent is produced from a toxicologically characterized compound. Another advantage of the instant invention is that the synthesis of 2-O desulfated heparin can be produced at commercially feasible levels.

Consideration of the specification, including the several figures and examples to follow will enable one skilled in the art to determine additional objects and advantages of the invention.

The present invention provides a medicament for the inhibition of neutrophil elastase and cathepsin G in mammals comprising a treatment effective amount of 2-O-desulfated heparin in a physiologically acceptable carrier. The physiologically acceptable carrier may be selected from the group consisting essentially of physiologically buffered saline, normal saline, and distilled water. In other embodiments of the invention, the effective ratio of 2-O-desulfated heparin to elastase is chosen to be greater than about 0.2, or effective the ratio of 2-O-desulfated heparin to cathepsin G is chosen to be greater than about 0.4.

The invention also provides a medicament comprising a dose of between 57.5 mg and 3.3435 grams of 2-O-desulfated heparin. Other doses include between 57.5 mg and 1.055 grams, between 180 mg and 3.345 grams and especially between 180 mg. and 1.055 grams. These doses are also provided in a physiologically acceptable carrier.

The present invention also provides a method for inhibiting neutrophil elastase and cathepsin G in mammals comprising administering a treatment effective amount of 2-O-desulfated heparin to a mammal. In preferred embodiments of the method of the invention, the treatment effective amount is administered by aerosolization or by intravenous (IV) injection. An effective dose for administration to a human, especially when used in an aerosol form, is a dose of between 57.5 mg and 3.3435 grams of 2-O-desulfated heparin. Other doses include between 57.5 mg and 1.055 grams, between 180 mg and 3.345 grams and especially between 180 mg and 1.055 grams. In other embodiments of the invention, the effective ratio of 2-O-desulfated heparin to elastase is greater than about 0.2, or the effective ratio of 2-O-desulfated heparin to cathepsin G is greater than about 0.4. Preferably, the medicament includes a physiologically acceptable carrier which may be selected from the group consisting of physiologically buffered saline, normal saline, and distilled water.

The present invention further provides a method of synthesizing 2-O-desulfated heparin comprising reducing heparin in solution and lyophylizing the reduced heparin solution. In a preferred embodiment, the pH of the reduced heparin solution is raised above 13.

BRIEF DESCRIPTION OF THE DRAWINGS

Reference to the following detailed description may help to better explain the invention in conjunction with the drawings in which.

DETAILED DESCRIPTION

The present invention may be understood more readily by reference to the following detailed description of specific embodiments and the Examples and Figures included therein.

As used in the claims, "a" can mean one or more.

Figure 1:
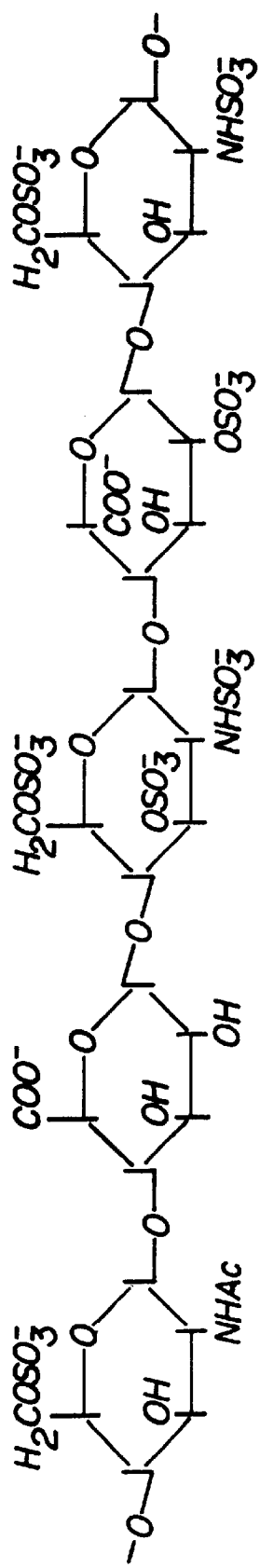
FIG. 1 shows a chemical formula of 2-O-desulfated α-L-iduronic acid in the pentasaccharide binding sequence of heparin.
Figure 2:
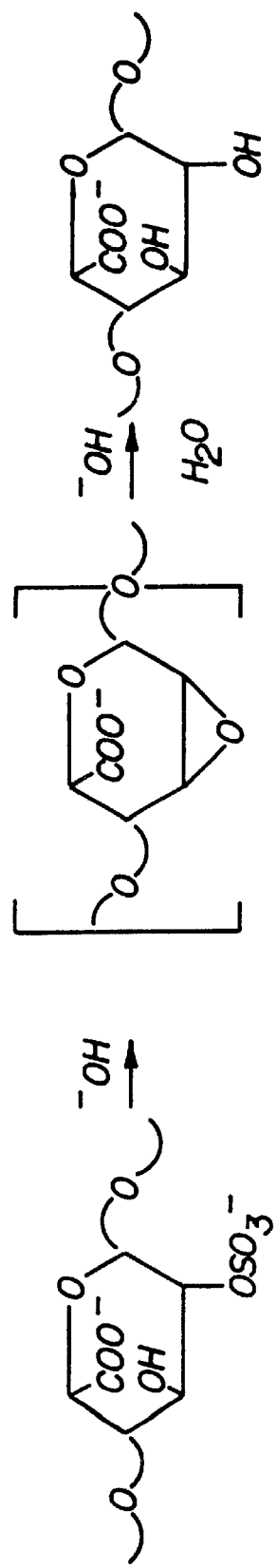
FIG. 2 shows a proposed reaction scheme for desulfating the 2-O-position of α-L-iduronic acid in the pentasaccharide binding sequence of heparin.

The removal of the 2-O-sulfate from α-L-iduronic acid in the pentasaccharide binding sequence of heparin, shown in FIG. 1, occurs due to the chemistry of sulfated carbohydrates in alkaline conditions which was first elucidated by E. G. V. Percival, *Quarterly Rev.*, (1949) 3:369–384, and reviewed in J. P. R. Turvey, *Adv. Carbohydrate Chem.*, (1965), 20:183–218. A sulfate group on a secondary hydroxyl group is susceptible to alkaline hydrolysis if there is an adjacent, trans, free hydroxyl group available for forming an epoxide intermediate as the sulfate is eliminated. This is shown in FIG. 2. For heparin, this reaction has been recently reported to occur with alkaline hydrolysis during lyophilization. (R. Rej, et al., *Thromb. Haemostas.* (1989) 61:540; and M. Jaseja, et al., *Can. J. Chem.* (1989) 67:1449–1456). Modification of these procedures by the present invention produced a heparin which is effective against elastase and cathepsin G, but without the anticoagulating properties of untreated heparin. Thus, 2-O-desulfated heparin can be used to treat Adult Respiratory Distress Syndrome (ARDS), cystic fibrosis (CF) and other pathologies associated with elastase and cathepsin G.

The present invention provides a method for inhibiting neutrophil elastase and cathepsin G in mammals comprising administering a treatment effective amount of 2-O-desulfated heparin or analog thereof to the mammal. Such a mammal can be a human. Also provided are novel analogs of 2-O-desulfated heparin. "Analog" includes compounds having the same functions as 2-O-desulfated heparin of anti-elastase and cathepsin G activity and minimal anticoagulant activity, including homologs that retain these functions. For example, substituents on the heparin polymer which are not essential to anti-elastase and cathepsin activity can be removed or altered by any of many means known to those skilled in the art, such as acetylation, deacetylation, decarboxylation, oxidation, etc. Additionally, low molecular weight 2-O-desulfated heparins can be utilized. Any analog can be readily assessed for these activities by known methods given the teachings herein. Useful 2-O-desulfated heparins can be made utilizing the method described herein.

The 2-O-desulfated heparin, or analog thereof, can be administered by aerosolization or by intravenous (IV) injection.

The instant method further comprises mixing the 2-O-desulfated heparin, or analog thereof, with a physiologically acceptable carrier for administration. Any physiologically acceptable carrier can be utilized, such as physiologically buffered saline, normal saline and distilled water. A treatment effective amount is that amount that causes a reduction in neutrophil elastase and cathepsin G.

The present invention further provides a medicament comprising a dose of between 57.5 mg and 3.3435 grams of 2-O-desulfated heparin. Other doses include between 57.5 mg and 1.055 grams, between 180 mg and 3.345 grams and especially between 180 mg. and 1.055 grams. This medicament can be in a physiologically acceptable carrier.

Analogs of 2-O-desulfated heparin, as previously described, can include 2-O-desulfated heparin that has been additionally modified, either prior to or after 2-O-desulfation, by any of several means standard in the art, such that they retain their elastase and cathepsin G activity, as well as their low anticoagulant activity. Such modifications can include acetylation, deacetylation, oxidation and/or decarboxylation, for example. Several modifications of heparin have been developed for their decreased anticoagulant activities.

For example, periodate oxidation (U.S. Pat. No. 5,250, 519, Conrad and Yuchuan) is a known oxidation method that produces an oxidized heparin having reduced anticoagulant activity. Other oxidation methods, also well known in the art, can be used. Additionally, for example, decarboxylation of heparin is also known to decrease anticoagulation activity, and such methods are standard in the art. Furthermore, low molecular weight heparins are known in the art to have decreased anticoagulant activity, and they are produced by standard techniques. Thus, "analogs" of 2-O-desulfated heparin can include, for example, periodate-oxidized 2-O-desulfated heparin, decarboxylated 2-O-desulfated heparin, acetylated 2-O-desulfated heparin, deacetylated 2-O-desulfated heparin, deacetylated, oxidized 2-O-desulfated heparin and low molecular weight 2-O-desulfated heparin. Many other analogs will be apparent to those of skill in the art, given the teachings provided herein.

The present invention further provides a method of synthesizing 2-O-desulfated heparin comprising reducing heparin in solution and drying, lyophilizing or vacuum distilling the reduced heparin solution. One can place the starting heparin in, for example, water, or other solvent, as long as the solution is not highly alkaline. A typical concentration of heparin solution can be from 1 to 10 percent heparin. The heparin used in the reaction can be obtained from numerous sources, known in the art, such as porcine intestine or beef lung. One can utilize heparin that has been modified in any of a number of ways known to those of skill in the art discussed above, i.e., a heparin analog, to create a 2-O-desulfated heparin analog.

The reduced heparin solution can be dried, or lyophylized or the solvent can be vacuum distilled. Lyophilization or vacuum distillation of the solvent is preferred. Generally, lyophilization is utilized. The heparin can be reduced by incubating it with a reducing agent, such as sodium borohydride, catalytic hydrogen, or lithium aluminum hydride. A preferred reduction of heparin is performed by incubating the heparin with sodium borohydride. Generally, about 10 grams of $NaBH_4$ can be used per liter of solution, but this amount can be varied as long as reduction of the heparin occurs. Additionally, other known reducing agents can be utilized. The incubation can be achieved over a wide range of temperatures, taking care that the temperature is not so high that the heparin caramelizes. A suggested temperature range is about 15–30° C., or even about 20–25° C. The length of the incubation can also vary over a wide range, as long as it is sufficient for reduction to occur. For example, several hours to overnight (i.e., about 4 to about 12 hours) can be sufficient. However, the time can be extended to over several days, for example, exceeding about 60 hours.

Additionally, the method further comprises raising the pH of the reduced heparin solution to 13 or greater by adding a base capable of raising the pH to 13 or greater to the reduced heparin solution. The pH can be raised by adding any of a number of agents including hydroxides, such as sodium, potassium or barium oxide. A preferred agent is sodium hydroxide (NaOH). Even once a pH of 13 or greater has been achieved, it can be beneficial to further increase the concentration of the base. For example, it is preferable to add NaOH to a concentration of about 0.25M to about 0.5M NaOH. This alkaline solution is then dried, lyophilized or vacuum distilled.

The instant invention additionally provides aerosol particles comprising a physiologically acceptable carrier and an effective amount of 2-O-desulfated heparin or analog thereof. The particles can consist essentially of particles less than 10 microns and preferably less than 5 microns.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected drug in combination with a pharmaceutically acceptable carrier and, in addition, may include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Liquid compositions can be aerosolized for administration. Actual methods of preparing such dosage forms are known, or will be apparent, to those skilled in this art; for example, see *Remington's Pharmaceutical Sciences*, E. W. Martin, (ed.), Mack Publishing Co., Easton, Pa.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

By "pharmaceutically acceptable" is meant a material that is not biologically or otherwise undesirable, i.e., the material may be administered to an individual along with the 2O-desulfated heparin or heparin analog without causing any undesirable biological effects or interacting in a deleterious manner with any of the other components of the pharmaceutical composition in which it is contained.

The instant invention additionally provides aerosol particles comprising a physiologically acceptable carrier and an effective amount of 2-O-desulfated heparin or analog thereof. The particles can consist essentially of particles less than 10 microns, and preferably less than 5 microns in size.

The present invention is more particularly described in the following examples which are intended as illustrative only since numerous modifications and variations therein will be apparent to those skilled in the art.

EXAMPLES

Example I

Partial N-Desulfation of Heparin

Porcine intestinal mucosal heparin (Scientific Protein Laboratories, Waunakee, Wis.) was converted to heparinic acid by passing a 4% aqueous solution over a cation exchange resin column, Dowex 50W x 8X ($H^+$). The solution of heparinic acid was then kept at 55° C. for 72 hours in a standard chemical reflux apparatus to remove approximately 70% of N-sulfates, as reported by L. Levy et al., *Proc. Soc. Exp. Biol. Med.* (1962) 109:901–905 and E. Sache et al., *Thromb. Res.* (1989) 55:247–258. The N-desulfated heparin was recovered by passing the solution over IR-400 resin ($OH^-$) to remove excess $SO_4^=$ followed by adjustment of pH to 7.0 and lyophilization.

Example II

Interaction of Partially N-Desulfated Heparin with HLE

The inhibition of HLE by partially N-desulfated heparin of Example I was measured by incubating a constant amount of HLE (100 pmol) with increasing amounts of partially N-desulfated heparin (10–50 pmol, I:E ratio 0.1–0.5) for 30 minutes at 25° C. in 500 microliters of Hepes buffer (0.125 M, 0.125% Triton-X-100, pH 7.5) diluted to the final volume of 900 microliters. The remaining enzyme activity was measured by adding 100 microliters of 3 mM N-Suc-Ala-Ala-Val-NA (Sigma Chemicals, St. Louis, Mo., made in dimethylsulfoxide [DMSO]) and reading the absorbance of the proteolytically released chromogen 4-Nitroaniline at 405 nm. The percentage of inhibition was calculated based on enzyme activity without inhibitor.

The results of the interaction of partially N-desulfated heparin and heparin with HLE are shown in Table I.

TABLE I

PERCENT INHIBITION OF HLE

| | Substrate Inhibitor[a] | |
|---|---|---|
| Ratio I:E | H | NDH |
| 0.1:1 | 53 | 29 |
| 0.2:1 | 79 | 37 |
| 0.3:1 | 88 | 37 |
| 0.4:1 | 90 | 49 |
| 0.5:1 | 91 | 50 |

[a]H = Heparin; NDH = Heparin partially N-desulfated according to Example I

As shown in Table I, heparin significantly inhibited human leukocyte elastase (HLE) at I:E ratios of greater than 0.2. In contrast, heparin partially N-desulfated according to Example I had greatly reduced ability to inhibit HLE, even at I:E ratios of 0.5. Thus, the activity of heparin as an inhibitor of HLE was substantially diminished by even partial desulfation of the polysaccharide by this treatment commonly used to eliminate the anticoagulant effect of heparin. These results were consistent with previously discussed teachings in the art suggesting that desulfation destroys the activity of heparin as an inhibitor of HLE and cathepsin G.

Example III

2-O-Desulfation of Heparin:

An aqueous solution of 0.4% porcine intestinal mucosal heparin (Scientific Protein Laboratories, Waunakee, Wis.) (4 mg/ml) was adjusted to pH 13.0 with 0.1 N NaOH, frozen, then lyophilized in 40 ml aliquots. After the product was redissolved in water and passed over an Amberlite IR-120 plus (H+) cation exchange resin to remove excess sodium hydroxide, final pH was adjusted to 7.0, and the solution was passed through a 0.2 micron Millipore filter by vacuum filtration to ensure bacterial sterility prior to final re-lyophilization to dryness.

Example IV

Effect of 2-O-Desulfated Heparin on Blood Coagulation:

The anti-coagulant potential of the desulfated heparin from Example III was studied by determining its effect on the activated partial thromboplastin time (APPT) in vitro. The test was performed in the usual fashion used to monitor the anti-coagulant effect of heparin clinically in patients. The test used 0.1 and 1.0 mg/ml heparin or heparin, 2-O-desulfated according to Example III, added to human test serum in vitro.

TABLE II

| | Control | Heparin | | 2-O-Desulfated Heparin | |
|---|---|---|---|---|---|
| Conc. (mg/ml) | 0 | 1.0 | 0.1 | 1.0 | 0.1 |
| Time to Clot Formation (sec) | 35–45 | >150 | 80 | 42 | 38 |

The 2-O-desulfated heparin from Example III was also studied to determine whether plasma dilutions of 0.1 mg/ml heparin or heparin, desulfated according to Example III, inhibited factor Xa, prolonging test time in an assay for Xa activity utilizing plasma treated with Russell viper venom.

TABLE III

Anti-factor Xa Activity

| Dilution | Control Plasma | Heparin | 2-O-Desulfated Heparin |
|---|---|---|---|
| 1:2 |  | >8 min. | 42 sec. |
| 1:10 |  | >7 min. | 33 sec. |
| 1:100 |  | 42 sec. | 32 sec. |
| 1:1000 |  | 32 sec. | 32 sec. |
| 0 | 35 sec. |  |  |

In contrast to heparin, the heparin desulfated according to Example III showed little ability to prolong the APTT and little antifactor Xa activity. Thus, the 2-O-desulfated heparin showed a much reduced anti-coagulant activity when compared to non-desulfated heparin.

Example V

Interaction of 2-O-Desulfated Heparin with HLE and Cathepsin G:

The inhibition of HLE by 2-O-desulfated heparin of Example III was measured by incubating a constant amount of HIE (100 pmol) with increasing amounts of 2-O-desulfated heparin (10–60 pmol, I/E ratio 0.1–0.6) for 30 minutes at 25° C. in 500 microliters of Hepes buffer (0.125 M, 0.125% Triton-X-100, pH 7.5) diluted to the final volume of 900 microliters. The remaining enzyme activity was measured by adding 100 microliters of 3 mM N-Suc-Ala-Ala-Val-NA (Sigma Chemicals, St. Louis, Mo., made in dimethylsulfoxide [DMSO]) and reading the absorbance of the proteolytically released chromogen 4-Nitroaniline at 405 nm. The percentage of inhibition was calculated based on enzyme activity without inhibitor.

The inhibition of cathepsin G by 2-O-desulfated heparin of Example III was measured as described above, except that the substrate was 3 mM Suc-Ala-Ala-Pro-Phe-pNA (Sigma Chemical, in DMSO).

Also, bovine ligament elastin was prepared according to B. C. Starcher, Anal. Biochem. (1976) 74:441–447. The elastin was assessed for purity by amino acid analysis. Its degradation was assayed using elastin radiolabeled with $^3$H-NaBH$_4$, following the methods described in P. J. Stone, et al., Methods Enzymol. (1982) 82:588–605. The tritiated powdered elastin was homogenized and washed in phosphate buffered saline (PBS), pH 7.4 just before use to remove unincorporated radioactivity. A constant amount of human leukocyte elastase (HLE) (67 pmol) was pre-incubated with increasing amounts of 2-O-desulfated heparin (6.7–134 pmol) at 37° C. for 30 minutes in a final volume of 1.0 ml Hepes buffer (0.125 M, 0.125% Triton-X-100, pH 7.5). An aliquot of 900 microliters of each reaction mixture was incubated with 5 mg $^3$H-elastin and 100 microliters of 0.9% saline at 37° C. Solubilized peptides were separated from the elastin suspension by filtration through medium-porosity filter paper. The rate of degradation was determined by quantifying the solubilized $^3$H peptides.

The results of the interactions of 2-O-desulfated heparin and heparin with HLE and cathepsin G are shown in Table IV.

TABLE IV

PERCENT INHIBITION

| | HLE | | | | Cathepsin G | |
|---|---|---|---|---|---|---|
| | Substrate[a] | | | | | |
| | A | | B | | C | |
| | Inhibitor[b] | | | | | |
| Ratio I:E | H | ODH | H | ODH | H | ODH |
| 0.1:1 | 23 | 20 | 72 | 73 | 31 | 14 |
| 0.2:1 | 81 | 74 | 95 | 77 | 49 | 54 |
| 0.3:1 | 88 | 84 | — | — | — | — |
| 0.4:1 | 87 | 85 | 92 | 72 | 67 | 56 |
| 0.5:1 | 87 | 84 | 94 | 85 | — | — |
| 0.6:1 | 99 | 100 | — | — | — | — |
| 0.8:1 | — | — | — | — | 78 | 69 |
| 1.0:1 | — | — | 97 | 85 | 76 | 69 |
| 2.0:1 | — | — | 97 | 84 | 76 | 67 |

[a]A = N—Suc—Ala—Ala—Val—NA; B = $^3$H-Elastin; C = Suc—Ala—Ala—Pro—Phe—pNA.
[b]H = Heparin; ODH = 2-O-Desulfated Heparin according to Example III As is shown in Table IV, ratios of inhibitor to substrate (I:E) of greater than 0.2 produces significant inhibition of human leukocyte elastase (HLE), I:E ratios of greater than 0.4 also provides significant inhibition of cathepsin G by both heparin and heparin 2-O-desulfated according to Example III. Throughout the range of ratios, there is very little difference between the effective inhibition of heparin and the heparin 2-O-desulfated according to Example III. Thus, the 2-O-desulfated heparin provides substantially the same inhibition as does the non-desulfated heparin. In addition, the 2-O-desulfated heparin showed little anticoagulant activity. This is in contrast to the unmodified heparin which is a very active anticoagulation agent.

Example IV

In Vivo Studies:

The ability of desulfated heparin to prevent human leukocyte elastase (HLE)-mediated lung injury was assessed in female golden Syrian hamsters (Harlan Industries, Indianapolis, Indiana) weighing 90 to 110 g. Phenobarbital-anesthetized hamsters were injected intratracheally with 0.25 ml sterile 0.9% saline (NS), 0.25 ml NS containing HLE (100 μg), or 0.25 ml NS containing 500 μg of heparin (Sigma) or 2-O-desulfated heparin according to Example III followed by 0.25 ml NS with HLE. Animals were killed by exsanguination 24 hours after treatment. The throat was opened and lungs dissected en bloc. The trachea was cannulated with polyethylene tubing and lavaged with five sequential aliquots of 3 ml NS. Lavage fluid was centrifuged at 200 Xg for 10 minutes. The resulting cell pellet was re-suspended in 1 ml Hank's balanced salt solution (HBSS) for performing cell count and differentials. The supernatant was assayed for protein and hemoglobin, as indices of acute injury. The results are shown in Table V and in FIGS. 3–5.

TABLE V

| Injected Solution[b] | pMN[a] (×10$^5$ Cells) | Total Hemoglobin (mg) | Protein (mg/ml) |
|---|---|---|---|
| Control | 0.95 | 0.396 | 35.08 |
| 0.25 ml NS | (0.443) | (0.215) | (0.111) |
| HLE | 16.3 | 8.15 | 100.69 |

TABLE V-continued

| Injected Solution[b] | pMN[a] (×10⁵ Cells) | Total Hemoglobin (mg) | Protein (mg/ml) |
|---|---|---|---|
| (100 μg) | (0.744) | (0.53) | (0.98) |
| HLE + H (100 μg + 500 μg) | 10.83 (0.452) | 0.867 (0.439) | 41.06 (0.114) |
| HLE + ODH (100 μg + 500 μg) | 9.83 (0.86) | 1.5 (0.23) | 65.80 (0.659) |

[a]PMN = polymorphonuclear leukocyte
[b]HLE = human leukocyte elastase; H = heparin; ODH = 2-O-desulfated heparin according to Example III Both heparin and 2-O-desulfated heparin, according to Example III, were potent inhibitors of elastase induced injury in vivo.

The 2-O-desulfated heparin from Example III has been tested for toxicity. Other sulfated polysaccharide inhibitors of elastase and cathepsin G, such as dextran sulfate, produced hemorrhage into lung air sacs (alveolar hemorrhage) when injected into rats intratracheally in doses as low as 0.5 mg/kg. The 2-O-desulfated heparin from Example III produced no alveolar hemorrhage in rats even in intratracheal doses of 10 mg/kg.

Human studies

The use of 2-O-desulfated heparin in a human subject can be performed as follows: For treatment of a patient with cystic fibrosis, a dose that provides a 5:1 ratio of inhibitor to protease (as described in Example IX below) is prepared and administered as an aerosol. In a patient producing 50 ml of sputum per day and producing average amounts of leukocyte elastase in the sputum, this dose can be about 255 mg of 2-O-desulfated heparin administered by a nebulizer over a course of 24 hours. Elastase and cathepsin G levels in the patient's sputum can be monitored during treatment.

Example VII

Attempted 2-O-Desulfation of Heparin (larger scale):

50 gm

To produce the 2-O-desulfated heparin of Example III in larger quantities, 50 gm quantities of porcine intestinal heparin were suspended in 1% (lot EM030992A1), 2% (EM030992A2), 3% (EM030992A3), 4% (EM030992A4) or 5% (EM030992A5) aqueous solutions alkalinized to pH 13 with addition of sodium hydroxide. Preliminary experiments demonstrated that the pH of 12.5–12.8 as taught by Jaseja et al failed to result in a decrease of USP anticoagulant activity for the final product. The 1–5% heparin solutions were lyophilized and excess base was eliminated as in Example III. Table VI shows that when tested as in Example V using the chromogenic substrate N-Suc-Ala-Ala-Val-NA, these heparin modifications retained their ability to inhibit HLE.

TABLE VI

HEPARIN-ANALOGS INTERACTION WITH HLE:
% HLE Inhibition

| IE Ratio | Heparin | EMO30 9992A1 | EMO30 9992A2 | EMO30 9992A3 | EMO30 9992A4 | EMO30 9992A5 | MM0107 692 |
|---|---|---|---|---|---|---|---|
| 0.1:1 | 58 | 40 | 35 | 23 | 23 | 24 | 29 |
| 0.2:1 | 72 | 56 | 52 | 40 | 36 | 41 | 32 |
| 0.3:1 | 83 | 74 | 70 | 53 | 51 | 58 | 50 |
| 0.4:1 | 88 | 85 | 83 | 72 | 71 | 65 | 59 |
| 0.5:1 | 93 | 83 | 83 | 81 | 81 | 81 | 62 |
| 1:1 | 98 | — | — | — | — | — | 69 |
| 1.5:1 | 98 | — | — | — | — | — | — |
| 2:1 | 98 | — | — | — | — | — | 93 |
| 3:1 | — | — | — | — | — | — | 95 |

1000 gm

Figure 6:
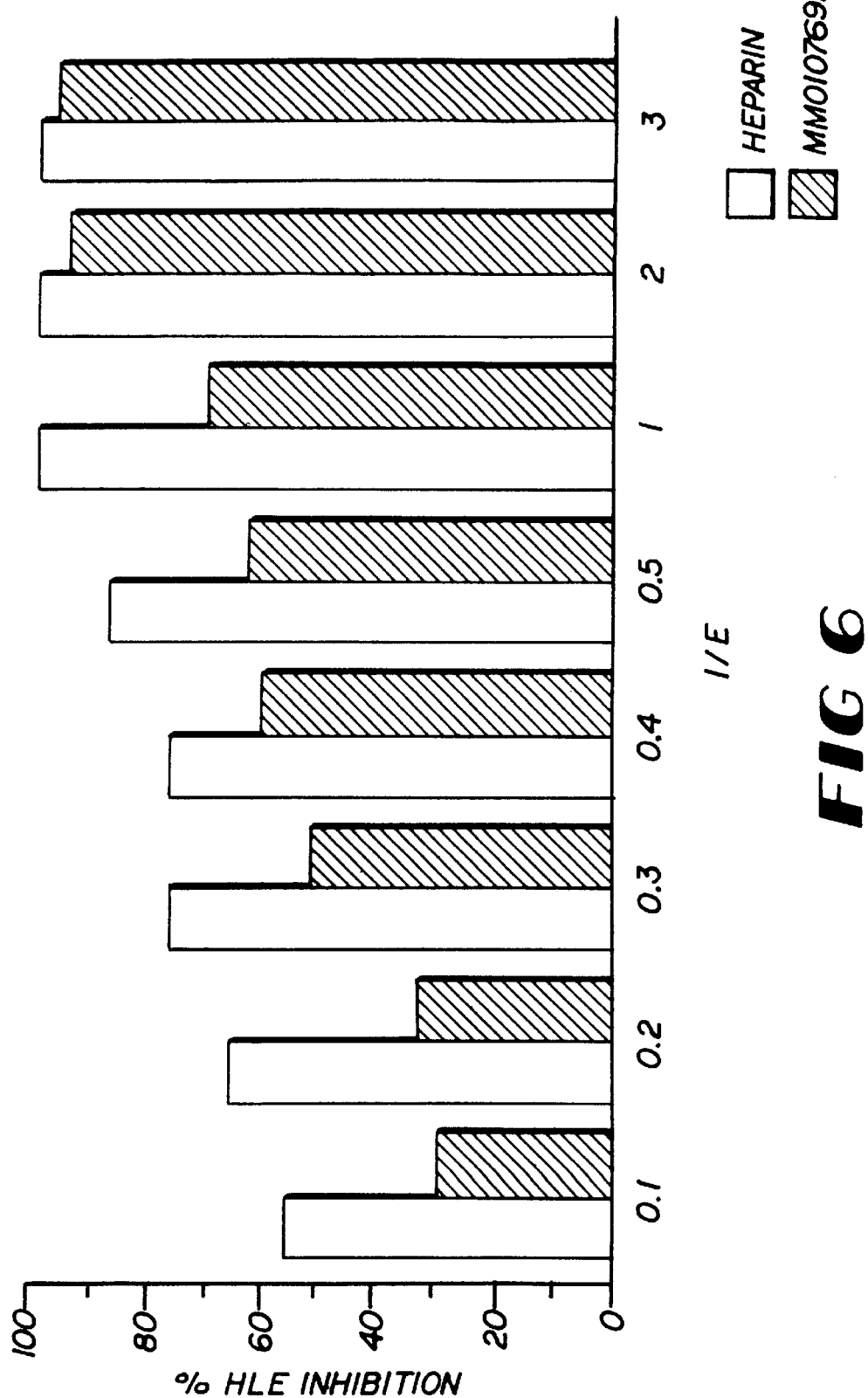
FIG. 6 shows a graph of the percent of HLE inhibition obtained with the indicated ratio of inhibitor (I) to enzyme (E). The inhibitors used are heparin (on the left in each ratio graph) and MM0107692 (on the right)

This same reaction process was then attempted on a commercially practical scale. 1000 gm of sodium heparin from porcine intestinal mucosa was dissolved in 65 L deionized water (1.5% concentration) and alkalinized to pH 13.1 with addition of 50% sodium hydroxide. The mixture was agitated for 2–3 hours, followed by lyophilization and elimination of excess base as previously described. The resulting product (MM0107692) had less than 10 units/mg USP anticoagulant activity, compared to 170 units/mg for the starting heparin. However, MM0107692 was a coarse brown granular substance instead of a fine white powder as the starting heparin. Table VI above and FIG. 6 also demonstrate that compared to the starting heparin, MM0107692 had greatly diminished ability to inhibit HLE. Thus, the chemical reaction taught by Jaseja et al., even modified to a pH of greater than 13 to result in decreased anticoagulant activity for the final product, does not lend itself to production on a commercially feasible scale of an alkaline hydrolyzed heparin that is an effective inhibitor of HLE.

Example VIII

Successful Preparation of 2-O-Desulfated Heparin (large scale):

Experiments were undertaken to discover a method for producing commercially practical quantities of 2-O-desulfated heparin. It was found that employing two important and unique modifications to the reaction of Jaseja et al. resulted in the production of 2-O-desulfated heparin: (1) increasing the pH of the lyophilization mixture to greater than 13, and (2) adding a catalytic amount of an appropriate reducing substance, such as sodium borohydride. Experiments are outlined in Table VII.

TABLE VII

Starting Material: Heparin Sodium, Lot No. EM0307991; Anti-coagulant Activity = 173.0 u/mg; Galactosamine = <2.0%

| Lot No. | Grams Heparin | Water | NaHCO$^3$ | Grams NaBH$^4$ | NaOH | pH | Dialysis | Optional Rotation | USP Activity | Anti Xa Activity 1 mg per ml/0.1 mg per ml |
|---|---|---|---|---|---|---|---|---|---|---|
| HM0500393 | 100 | 1 L | — | 19 | 0.05M | 12 | Pelican | +55.2° | 138.6 | — |
| HM0500593 | 100 | 1 L | 6 gms | 9 | 0.05M | 12 | Pelican | +54.5° | 155.0 | — |
| HM0500793 | 100 | 1 L | 6 gms | 9 | 0.05M | 12 | No. Dial. | +50.7° | 155.2 | — |
| HM0502193 | 100 | 1 L | 6 gms | 9 | 0.50M | 13.2 | UF | +55° | 45.9 | 112/11.2 |
| HM0502303 | 100 | 1 L | 6 gms | 9 | 0.30M | 13.2 | UF | +63° | 58.1 | 146/14.2 |
| HM0502593 | 100 | 1 L | 6 gms | 20 | 0.20M | 13.2 | UF | +56.7° | 57.3 | 126/11 |
| HM0502993 | 100 | 2 L | 6 gms | 20 | 0.25M | 13.2 | UF | +59.6° | 62.0 | 60/6 |
| HM0503193 | 100 | 2 L | — | 20 | 0.25M | 13.2 | UF | +49° | 26.9 | 60/4 |
| HM0504493 | 100 | 1 L | — | 10 | 0.4M | 13.2 | UF | +52° | 44.7 | — |
| HM0504693 | 100 | 2 L | — | 20 | 0.5M | 13.15 | UF | +41° | <15 | — |
| HM0504893 | 50 | 1 L | — | 10 | 0.4M | 13.3 | UF | — | <15 | 50/3 |
| HM0505093 | 75 | 1 L | — | 10 | 0.4M | 13.3 | UF | — | 20.7 | 60/4 |
| HM0505293 | 100 | 1 L | — | 10 | 0.4M | 13.3 | UF | — | 34.7 | 70/5 |

Note:
Exp. 023 - The Heparin concentration was adjusted to 7.5% by diluting with water before raising pH >13.
UF = Ultrafiltration Heparin modifications HM0500393 through HM0505293 were made from the same lot of porcine intestinal mucosal sodium heparin having 173.0 units/mg USP anticoagulant activity (USP method) and approximately 150 units/mg anti-Xa activity (by amidolytic assay using commercially available chromogenic peptide substrate). Preparation of modifications began with dissolution of 50 to 100 gm heparin to 5–10% concentration in deionized water, followed by addition of sodium borohydride.

In the case of modifications HM0500593, HM0500793, HM0502103, HM0502393, HM0503593 and HM0502993, heparin was treated with sodium borohydride in the conventional manner known to those experienced in the art by alkalinizing the solution slightly to pH 8–9 with sodium bicarbonate (Conrad et al, U.S. Pat. No. 5,250,519 (Oct. 5, 1993)). In all other cases, sodium borohydride was added without slightly alkalinizing the solution (i.e., without sodium bicarbonate). After incubation with sodium borohydride for 12–24 hours at 20–25° C., sodium hydroxide was added to the final concentration listed and the mixture was lyophilized. Excess reducing agent was eliminated by a commercially conventional method, usually ultrafiltration.

Table VII shows that alkalinization to pH 12 failed to produce an alkaline hydrolyzed heparin with reduced anticoagulant activity (HM0500393, HM0500593, HM0500793). Anticoagulant activity was always reduced when pH was increased to greater than 13 prior to lyophilization, but reduction in USP and anti-Xa activity was greatest when final sodium hydroxide concentration was 0.25 to 0.5 M. Additionally, reduction in USP and anti-Xa activity was greatest when sodium borohydride was added without sodium bicarbonate (compare HM0502193, HM0502393, HM0502593 and HM06502993 (with sodium bicarbonate) to HM0503193, HM0504493, HM0504693, HM0504893, HM05093 and HM05293) (without sodium bicarbonate), though both groups of compounds displayed good HLE inhibitory activity. HIE inhibitory activity of the four modifications with the lowest USP anticoagulant activity was studied as in Example V. Table VIII shows that HM0504693, HM0504893, HM0505093 and HM0505293 all retain good HLE inhibitory activity for inhibitor to elastase ratios of 0.3 to 0.5:1 and above.

TABLE VIII

% HLE INHIBITION

| I:E | Heparin | HM0502993 | HM0503193 | HM0504693 | HM0504893 | HM0505093 | HM0505293 | HM0506394 |
|---|---|---|---|---|---|---|---|---|
| 0.1:1 | 27.000 | 28.000 | 33.000 | 19.700 | 2.000 | 0.000 | 3.000 | 30.000 |
| 0.2:1 | 51.000 | 35.000 | 49.000 | 35.900 | 30.000 | 21.000 | 16.000 | 49.000 |
| 0.3:1 | 91.000 | 79.000 | 78.000 | 91.500 | 38.000 | 36.000 | 71.000 | 61.000 |
| 0.5:1 | 97.000 | 92.000 | 95.000 | 97.500 | 73.000 | 86.000 | 64.000 | 85.000 |
| 1:1 | 98.000 | 97.000 | 97.000 | 98.100 | 95.000 | 96.000 | 96.000 | 96.000 |
| 2:1 | 99.000 | 98.000 | 98.000 | 98.300 | 96.000 | 97.000 | 96.000 | 98.000 |

Figure 7:
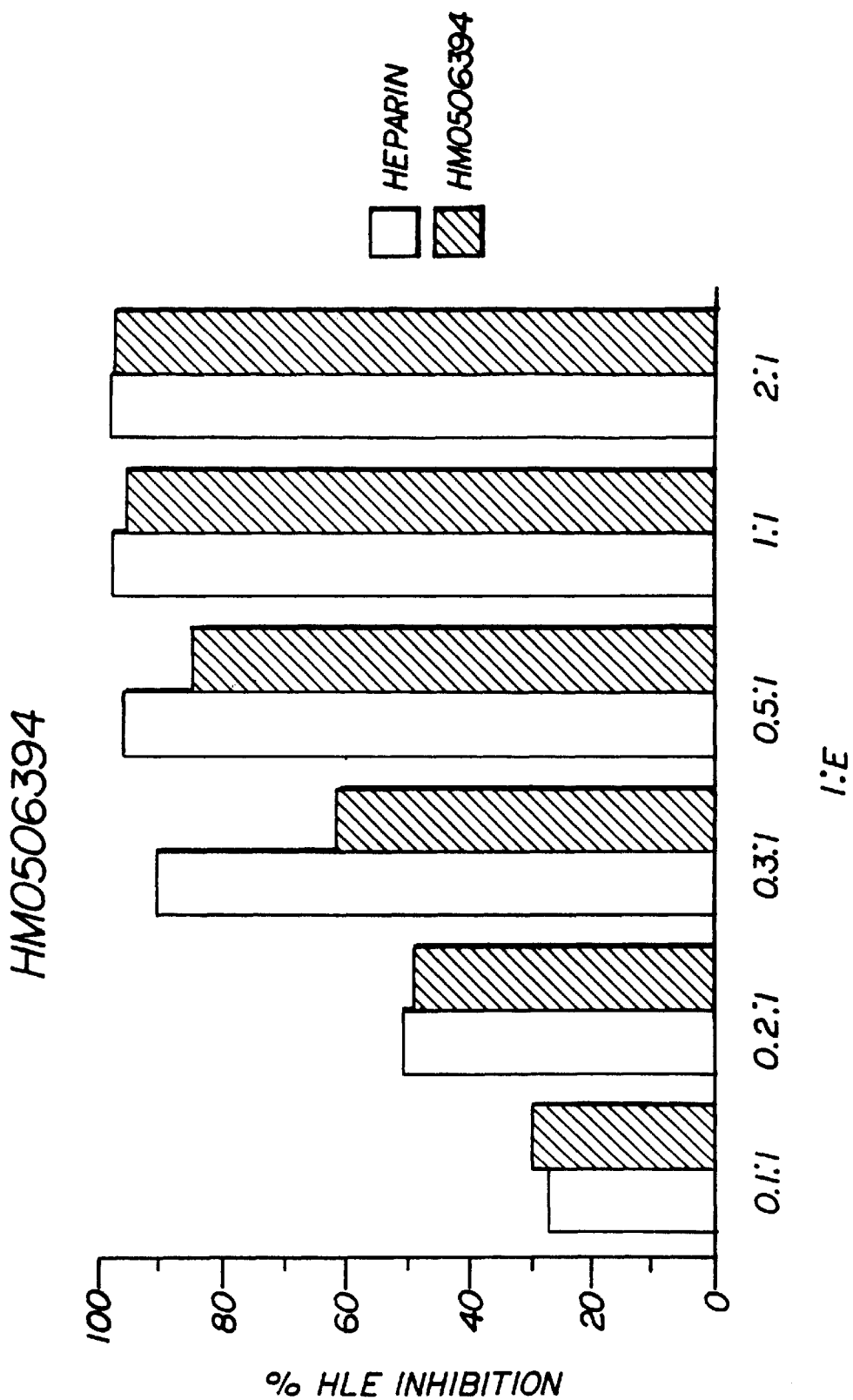
FIG. 7 shows a graph of the percent of HLE inhibition obtained with the indicated ratio of inhibitor (I) to enzyme (E). The inhibitors used are heparin (on the left in each ratio graph) and HM0506394 (on the right).

Based on findings in experiments of Table VII, production of 2-O-desulfated heparin by the new method was scaled up to a larger, more commercially practical scale. Heparin modification HM0506394 was made by adding 500 gm of porcine intestinal mucosal sodium heparin from lot EM0307991 to 10 L deionized water (5% final heparin concentration). Sodium borohydride was added to 1% final concentration and the mixture was incubated overnight at 25° C. Sodium hydroxide was then added to 0.4 M final concentration (pH greater than 13) and the mixture was lyophilized to dryness. Excess sodium borohydride and sodium hydroxide were removed by ultrafiltration. The final product was adjusted to pH 7.0, precipitated by addition of three volumes of cold ethanol and dried. The 2-O-desulfated heparin produced by this procedure was a fine crystalline slightly off-white powder with less than 10 USP units/mg anticoagulant activity. HM0506394 retained excellent HLE inhibitory activity, as shown in Table VIII and FIG. 7.

The alkaline hydrolyzed heparin having reduced anticoagulant activity, but retaining anti-elastase activity, produced according to Example III or Example VIII, can be used to treat respiratory diseases such as emphysema, chronic bronchitis, Adult Respiratory Distress Syndrome (ARDS) and cystic fibrosis by administration to the respiratory tree directly as an aerosol. A dose of from about 10 to about 100 mg of 2-O-desulfated heparin dissolved in 3 ml of sterile 0.9% saline can be aerosolized into the lung about every 6 hours (or about 4 times daily) using any common clinically available aerosol device (such as a Devilbiss or Acorn Nebulizer) attached to a positive pressure source (either compressor or compressed air or oxygen) to generate aerosols of particles less than 10 microns mass median diameter.

The lower doses can be effective for diseases such as chronic bronchitis, whereas the higher doses can be needed for cystic fibrosis, in which the levels of elastase in respiratory secretions are much higher.

For treatment of diseases of ischemia-reperfusion such as myocardial infarction and stroke, the 2-O-desulfated heparin can be administered intravenously (IV) by continuous infusion. After a bolus loading dose of 0.5 mg/kg intravenously, 2.5–5.0 mg/kg of 2-O-desulfated heparin is mixed with 250–500 ml of 5% dextrose, 0.45% NaCl or 0.9% NaCl and infused continuously over 24 hours to maintain a constant blood level of drug within the vascular system.

Example IX

Inhibition of Elastase and Cathepsin G Activity Treatment:

The best measurements of free leukocyte elastase and cathepsin G activity in cystic fibrosis sputum are from Goldstein and Doring, Am Rev. Respir. Dis., 1986; 134:49–56, who reported 96.1±91.7 µg/ml human leukocyte elastase (ranging from 22 to 398 µg/ml) and 5.9±6.0 ug/ml cathepsin G (ranging from 1 to 24 ug/ml). However, the Goldstein and Doring measurements were made before introduction of recombinant deoxyribonuclease I (rDNase) as a new adjunctive therapy for cystic fibrosis. See Hubbard et al., New Eng. J. Med (1992) 326:812–815; Ranasinha et al., Lancet, (1993) 342:199–202; Ramsey et al, Am. Rev. Respir. Dis., (1993) 148:145–151; Shak et al, Proc. Nat'l Sci. USA, (1990) 87:9188–9192. rDNase does not work against the primary inflammatory process but liquefies thick purulent sputum and facilitates its lung clearance by lysing the DNA (derived from disintegrated inflammatory cells) that contributes to its tenacious and viscous nature, Shak et al., Proc. Nat'l Sci. USA (1990) 87:9188–9192. Kueppers and Fiel, Am. Rev. Respir. Dis. (1993) 147:A563, have recently shown that DNA in purulent airway secretions also binds up considerable quantities of leukocyte elastase and cathepsin G. When cystic fibrosis sputum is treated with rDNase, levels of catalytically active leukocyte elastase rise three-fold and those of cathepsin G increase six-fold. Kueppers and Fiel, Am. Rev. Respir. Dis. (1993) 147:A563. In a rDNase treated cystic fibrosis patient, the levels of leukocyte elastase and cathepsin G that would require neutralization by an anti-elastase therapy could be-three-fold higher for elastase (or up to 3×398=1194 ug/ml for the peak range reported by Goldstein and Doring).

Therefore, the level of leukocyte elastase requiring neutralization could vary from a low of 22 ug/ml, average of 96 ug/ml and high of 398 ug/ml, Goldstein and Doring, in a patient not receiving rDNase treatment, to a low of 66 ug/ml, average of 288 ug/ml and a peak of 1194 ug/ml in a rDNase treated subject. The level of cathepsin G requiring neutralization could vary from a low of 1 ug/ml, average of 6 ug/ml and peak of 24 ug/ml (Goldstein and Doring) in a patient not receiving rDNase treatment, to a low of 6 ug/ml, an average of 36 ug/ml and a peak of 177 ug/ml in a patient receiving rDNase.

There is no way to accurately measure the entire volume of airway secretions in a live patient. However, the amount of sputum expectorated daily by cystic fibrosis patients using the most efficient chest physiotherapy technique averages 50 grams per 24 hours. Pflegler, et al., Lung (1992) 170:323–330. Well over 90% of tissue weight is water. Therefore, cystic fibrosis patients can be said to produce on the average about 50 ml sputum per day.

2-O-desulfated heparin can be delivered to the lungs by inhalation of an aerosol from an ultrasonic or jet nebulizer generating respirable particles less than 5 microns in mass median aerodynamic diameter (MMAD). While the exact percentage of aerosol actually reaching the lungs varies according to the type of jet or ultrasonic nebulizer used, about 10 percent of the dose in the nebulizer actually reaches the lungs. Newman, S. P., "Therapeutic Aerosols, in Aerosols in the Lung," Clinical and Experimental Aspects, S. W. Clarke and D. Pavia, eds., Butterworths: London (1984) pp. 197–224. Therefore, a patient will need to be treated with a nebulizer dose that is ten times the drug actually needed for effective neutralization of leukocyte protease activity in the lung.

Figure 3:
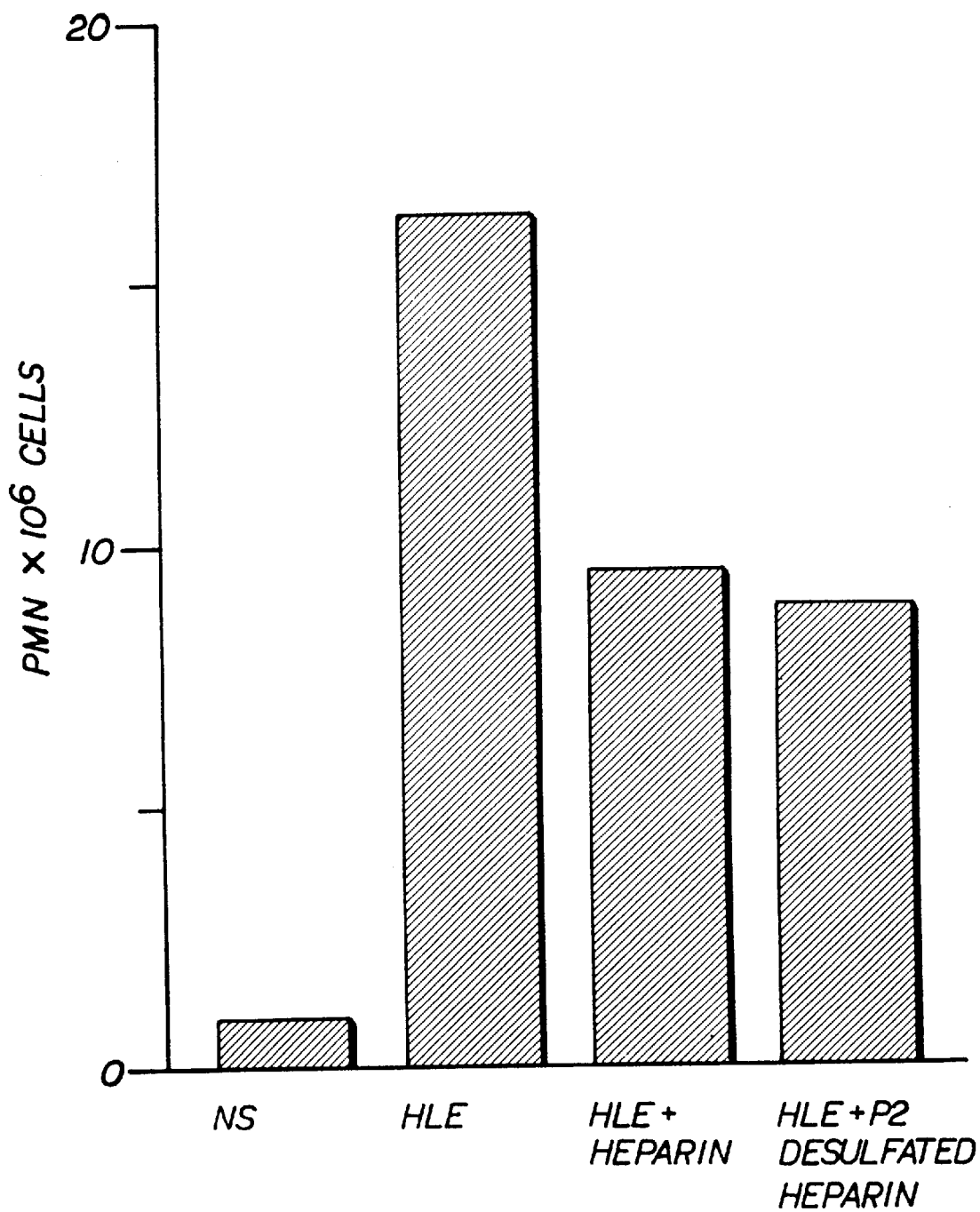
FIG. 3 shows a graph of the number of polymorphonuclear leukocyte (PMN) cells in the bronchoalveolar lavage fluid 24 hours after the administration of saline (control) human leukocyte elastase (HLE), HLE plus heparin, and HLE plus desulfated heparin.
Figure 4:
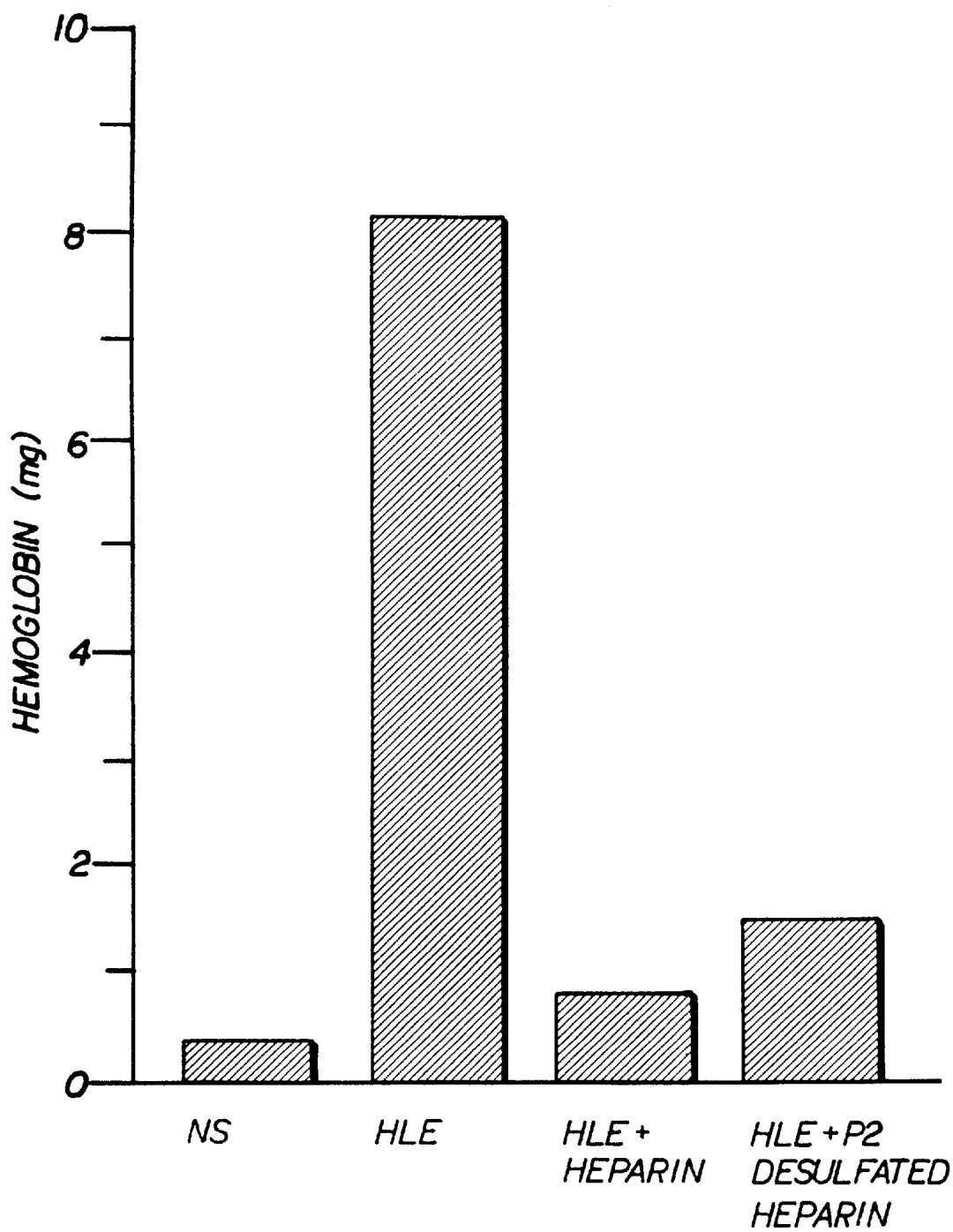
FIG. 4 shows a graph of the hemoglobin content measured in the bronchoalveolar lavage fluid 24 hours after the administration of saline (control), HLE, HLE plus heparin, and HLE plus desulfated heparin.
Figure 5:
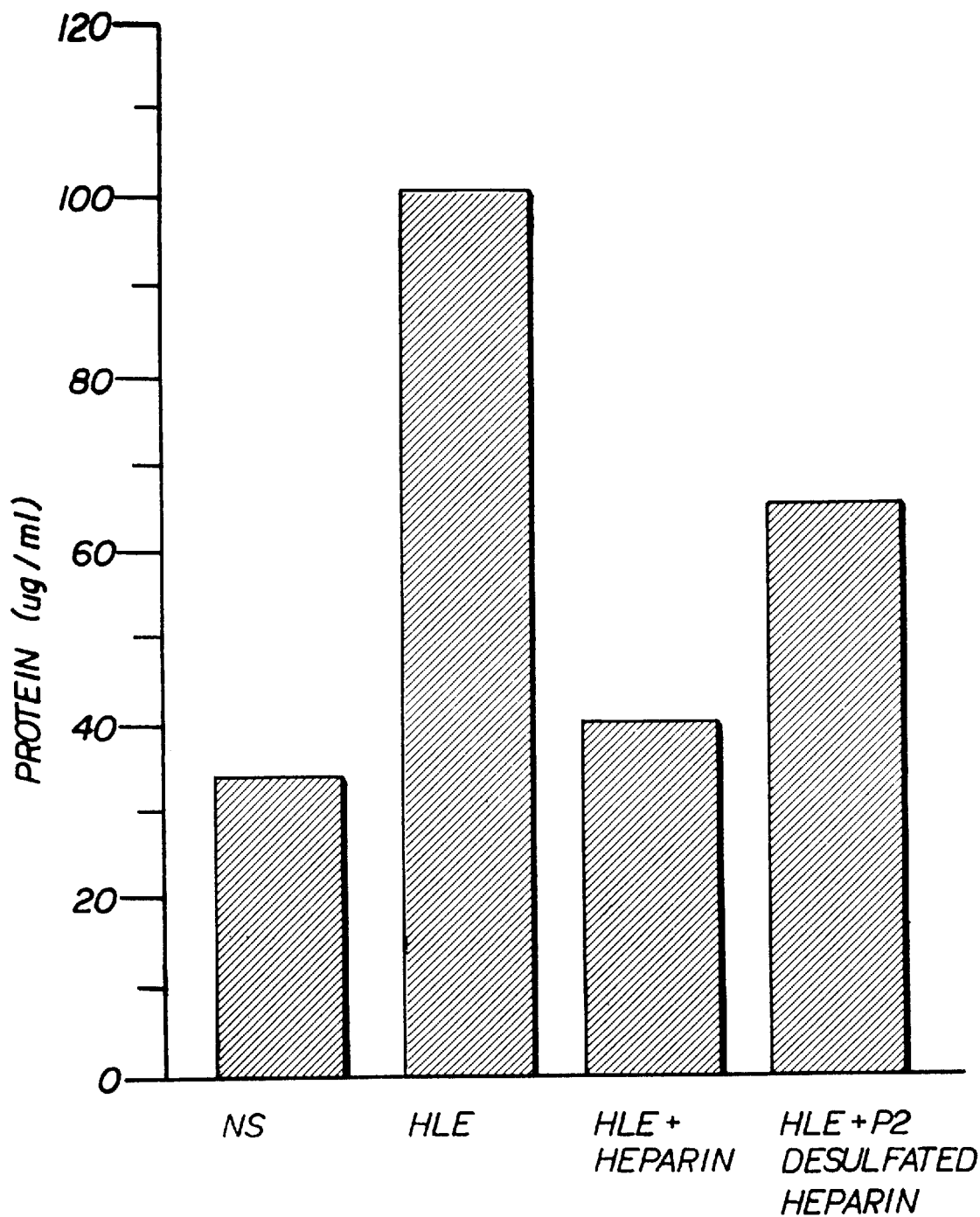
FIG. 5 shows a graph of the concentration of protein in the bronchoalveolar lavage fluid 24 hours after administration of saline (control), HLE, HLE plus heparin, and HLE plus desulfated heparin.

Tables IV and VIII indicate that effective in vitro inhibition of elastase and cathepsin G occurs at a molar ratio of inhibitor/protease of 0.3:1 and above. However, higher ratios than 0.3:1 are preferable in vivo because of binding of sulfated polysaccharides to components of normal lung. See Table 2, Rao et al, Am. Rev. Respir. Dis. (1990) 142:407–412. Therefore the ratio of inhibitor/protease for effective neutralization of protease and prevention of injury in the whole organism can be determined from in vivo experiments. Example VI provides these experiments. Table V and FIGS. 3–5 demonstrate that inhibition of proteolytic lung injury from elastase in vivo is obtained by administration of 500 ug of 2-O-desulfated heparin for every 100 ug human leukocyte elastase, or an inhibitor/protease ratio of 5:1 (weight/weight). This same 5:1 inhibitor/protease ratio has proven the lower limit for inhibition of leukocyte elastase-mediated lung injury by other sulfated polysaccharides (FIGS. 2, 3 and 4, Rao et al). This ratio provides an element of prolonged protection over many hours (FIG. 3, reference 22). However, this 5:1 ratio does not completely prevent elastase mediated lung injury, indicating that lower ratios of inhibitor/elastase are not likely to be as effective.

Based on an average of 50 ml sputum per day, and a 5:1 (wt./wt.) ratio of inhibitor to protease and a 10% nebulizer efficiency, the following formula will be used to calculate the nebulizer does of 2-O-desulfated heparin:

([elastase ug/ml]+[cathepsin G ug/ml])×50 ml sputum/day=mg protease/24 hours mg protease/24 hours×5=effective inhibitory mg of 2-O-deulfated heparin effective inhibitory mg of 2-O-DH×10=nebulizer dose of 2-O-desulfated heparin To calculate the lower end dose in a patient not treated with rDNase, we use the lowest sputum concentrations of leukocyte elastase (22 ug/ml) and cathepsin G (1 ug/ml) reported by Goldstein and Doring:

22 ug/ml+1 ug-ml=23 ug/ml×50=1.15 mg protease 1.15 mg protease/24 hr×5×10=57.5 mg of 2-O-desulfated heparin To calculate the average dose needed in a patient not treated with rDNase, we use the average sputum concentration of leukocyte elastase (96 ug/ml) and cathepsin G (6 ug/ml) reported by Goldstein and Doring:

96 ug/ml+6 ug/ml=102 ug/ml×50=5.1 mg protease 5.1 mg protease/24 hr×5×10=255 mg of 2-O-desulfated heparin To calculate the peak dose needed in a patient not treated with rDNase, we use the peak sputum concentration of leukocyte elastase (398 ug/ml) and cathepsin G (24 ug/ml) reported by Goldstein and Doring:

96 ug/ml+6 ug/ml=102 ug/ml×50=21.10 mg protease 21.10 mg protease/24 hr×5×10=1.055 g of 2-O-desulfated heparin To calculate the lower end dose in a patient receiving concurrent rDNase, we multiply the low sputum concentrations from Goldstein and Doring of leukocyte elastase (96 ug/ml) by 3 and cathepsin G (6 ug/ml) by 6 to adjust for the release of bound protease by rDNase (as taught by Kueppers and Fiel):

(22×3)+(1×6)=72 ug/ml×50=3.6 mg protease 3.6 mg protease/24 hr×5×10=180 mg of 2-O-desulfated heparin To calculate the average dose for a patient receiving concurrent rDNase, we multiply the average sputum concentrations from Goldstein and Doring of leukocyte elastase (96 ug/ml) by 3 and cathepsin G (6 ug/ml) by 6 to adjust for the release of bound protease by rDNase:

(96×3)+(6×6)=324 ug/ml×50=16.2 mg protease 16.2 mg protease/24 hr×5×10=810 mg of 2-O-desulfated heparin To calculate the high end dose for a patient receiving concurrent rDNase, we multiply the highest sputum concentration from Goldstein and Doring leukocyte elastase (398 ug/ml) by 3, and cathepsin G (24 ug/ml) by 6 to adjust for the release of bound protease by rDNase:

(398×3)+(24×6)=1338 ug/ml×50=66.9 mg protease 66.9 mg protease/24 hr×5×10=3.345 g of 2-O-desulfated heparin Therefore, the therapeutic dose of aerosolized 2-O-desulfated heparin needed per 24 hours to treat leukocyte elastase and cathepsin G mediated lung diseases such as cystic fibrosis can range from about 57.5 mg to 3.345 g, depending on many factors including the severity of lung inflammation and whether the patient is also treated with rDNase to liquefy lung secretions.

Based upon the above calculations, 2-O-desulfated heparin can be administered at lower or higher ratios of inhibitor to protease by scaling the dosages up or down. Additionally, the dose can be modified for individual subjects, based upon, for example, the individual's specific sputum production per day, or independent calculations of sputum concentrations of elastase and cathepsin G. Furthermore, as treatment progresses, the dose can be varied according to therapeutic effects observed with a specific dose.

The exact amount of such compounds required will vary from subject to subject, depending on the species, age, and general condition of the subject, the severity of the disease that is being treated, the particular compound used, its mode of administration, and the like. Thus, it is not possible to specify an exact activity promoting amount. However, an appropriate amount may be determined by one of ordinary skill in the art using only routine experimentation given the teachings herein.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A medicament comprising a partially desulfated heparin comprising desulfation at the 2-O position having a weight ranging from about 10 mg to about 100 mg made by the process comprising alkalinizing a solution containing heparin to pH 13 or greater, and a physiologically acceptable carrier.

2. The medicament of claim 1, wherein said carrier is physiologically buffered saline, normal saline, or distilled water.

3. The medicament of claim 1, wherein the heparin has a weight ranging from 2.5 mg/kg to 5.0 mg/kg.

4. The medicament of claim 1, wherein the heparin has a weight ranging from 0.5 mg/kg to 10 mg/kg.

5. The medicament of claim 1 comprising a dose of between 57.5 mg and 3.3435 grams of heparin.

6. The medicament of claim 1 comprising a does of between 57.5 mg and 1.055 grams of heparin.

7. The medicament of claim 1 comprising a dose of between 180 mg and 3.345 grams of heparin.

8. The medicament of claim 1 comprising a dose of between 180 mg and 1.055 grams of heparin.

9. The medicament of claim 1 in the form of aerosol particles consisting essentially of particles less than 10 microns.

10. The medicament of claim 1 in the form of aerosol particles consisting essentially of particles less than 5 microns.

11. The medicament of claim 1 in the form of aerosol particles.

12. The medicament of claim 1 in the form of an IV solution.

13. The medicament of claim 3 in the form of an IV solution.

14. The medicament of claim 1 for inhibiting neutrophil elastase or cathepsin G in a mammal, wherein the particularly desulfated heparin is in an inhibiting effective amount.

15. The medicament of claim 1 for treating emphysema, chronic bronchitis, adult respiratory distress syndrome, cystic fibrosis, or an ischemia-reperfusion related condition, wherein the partially desulfated heparin is in a treatment effective amount.

16. The medicament of claim 15, wherein the ischemia-reperfusion related condition arises from a myocardial infarction or a stroke.

17. The medicament of claim 14, wherein the mammal is a human.

18. The medicament of claim 1 wherein the heparin comprises partial desulfation at the 2-O position.

19. The medicament of claim 1 wherein the heparin comprises 3-O desulfation.

20. The medicament of claim 14 wherein the ration of partially desulfated heparin to elastase or cathepsin G is greater than about 0.2 or about 0.4 respectively.

21. A method of synthesizing 2-O-desulfated heparin comprising reducing heparin in solution and drying the reduced heparin solution.

22. A method of synthesizing 2-O-desulfated heparin comprising reducing heparin in solution and vacuum distilling the solvent from the reduced solution.

23. A method of synthesizing 2-O-desulfated heparin comprising reducing heparin in solution and lyophilizing the reduced heparin solution.

24. The method of claim 23, wherein the heparin is reduced by incubating the heparin with a sodium borohydride reducing agent.

25. The method of claim 23, further comprising raising the pH of the reduced heparin solution to 13 or greater.

26. The method of claim 23, further comprising adding sodium hydroxide to the reduced heparin solution to a sodium hydroxide concentration of about 0.25 M to about 0.5 M.

* * * * *

UNITED STATES PATENT AND TRADEMARK OFFICE
CERTIFICATE OF CORRECTION

PATENT NO. : 6,077,683
DATED : June 20, 2000
INVENTOR(S) : Kennedy

It is certified that error appears in the above-identified patent and that said Letters Patent is hereby corrected as shown below:

On the title page, [56] References Cited, U.S. Patent Documents, line 1, "3/1989" should read --4/1989--.

Column 9, line 22, "2O-desulfated" should read --2-O-desulfated--.

Column 12, line 39, in the sub-heading, "Example IV" should read --Example VI--; line 63, in TABLE V, line 2 of the second sub-heading, "(x10$^5$ Cells)" should read --(x10$^6$ Cells)--.

Column 13, in TABLE V-continued, line 2 of the second sub-heading, "(x10$^5$ Cells)" should read --(x10$^6$ Cells)--.

Signed and Sealed this

Twenty-ninth Day of May, 2001

Attest:

NICHOLAS P. GODICI

*Attesting Officer*        *Acting Director of the United States Patent and Trademark Office*